United States Patent [19]

Anderson

[11] Patent Number: 4,839,016
[45] Date of Patent: Jun. 13, 1989

[54] CURVED SURFACE CASSETTE/GEL SYSTEM

[75] Inventor: Norman L. Anderson, Washington, D.C.

[73] Assignee: Large Scale Biology Corporation, Rockville, Md.

[21] Appl. No.: 147,320

[22] Filed: Jan. 19, 1988

[51] Int. Cl.[4] .............................. G01N 27/26
[52] U.S. Cl. .................... 204/299 R; 204/182.8
[58] Field of Search ..................... 204/299 R

[56] References Cited

U.S. PATENT DOCUMENTS

| | | | |
|---|---|---|---|
| 3,594,263 | 7/1971 | Dwyer et al. | 161/160 |
| 3,759,773 | 9/1973 | Dwyer et al. | 156/280 |
| 4,088,561 | 5/1978 | Anderson | 204/299 |
| 4,169,036 | 9/1979 | Anderson et al. | 204/299 |
| 4,325,796 | 4/1972 | Hoefer et al. | 204/180 |
| 4,374,723 | 2/1983 | Vesterberg | 204/299 |
| 4,443,319 | 4/1984 | Chait | 204/299 R |
| 4,479,861 | 10/1984 | Hediger | 204/180 |
| 4,483,885 | 11/1984 | Chait et al. | 427/58 |
| 4,518,476 | 5/1985 | Delony | 204/299 R |
| 4,560,459 | 12/1985 | Hoefer | 204/182.8 |
| 4,594,064 | 6/1986 | Anderson | 204/299 |
| 4,650,556 | 3/1987 | Hashiue et al. | 204/182.7 |

OTHER PUBLICATIONS

J. I. Taylor & Sons, "Curv-X Cassette with a Curve Speeds Diagnosis", (Undated).
P. Horowitz et al., "The Use of Polyacrylamide Gel That Can Be Disassembled and Reassembled to Permit a Wide Variety of Electrophoretic Procedures with a Common Polymerization of History", *Electophoresis* 7, 534–535 (1986).
General Electric E006/08/12/13/14 Product Data Publication (Undated).

*Primary Examiner*—John F. Niebling
*Assistant Examiner*—Isabelle Rodriguez
*Attorney, Agent, or Firm*—Robbins & Laramie

[57] ABSTRACT

A curved-surface cassette/gel system is disclosed in which the walls of a cassette and the major surfaces of a slab-shaped electrophoresis gel in the cassette coact to substantially exclude liquid or gas from between either wall and the major surfaces of the gel. Exclusion is accomplished by exerting a normal force at all points on the walls of the cassette and at all points on the major surfaces of the gel. A curvature may be present in at least one wall of the cassette and in at least one major surface of the cassette. A cassette headpiece may be divided by septa which form an edge seal with the slab gel. The spaces formed between the septa function as wells into which sample materials may be placed.

25 Claims, 10 Drawing Sheets

CURVED SURFACE CASSETTE/GEL SYSTEM

BACKGROUND OF THE INVENTION

This invention relates to the field of gel electrophoresis, and in particular to cassette holders for slab-shaped electrophoresis gels and curved-surface cassette/gel systems. The invention may be incorporated into the multiple parallel slab gel electrophoresis system of U.S. Pat. No. 4,088,561, which is incorporated herein by reference.

Electrophoresis is a technique for separating molecules by virtue of their differential mobility in liquid medium under the influence of an electric field. Electrophoresis is usually performed in a gel medium to prevent convection in the fluid phase and the consequent loss of order and resolution. The gels used include polyacrylamide, agarose, and a variety of analogous substances.

Separations may be performed in gel rods, for individual samples, or in gel slabs, for a series of samples to be compared side-by-side or for two-dimensional separations. Typical dimensions of a gel slab for use in protein electrophoretic separation in the presence of sodium dodecyl sulfate (SDS) are 18 cm×18 cm×0.15 cm.

In many apparatus, including SDS-protein electrophoresis, the gel must be insulated on all surfaces except the two ends. A voltage is applied across these ends by means of contact between the gel ends and two buffer chambers containing electrodes, the anode in one chamber and the cathode in another. Such a configuration is usually implemented by surrounding the gel slab with an insulating cassette consisting of two sheets of insulator and insulating side spacers, forming a rectangular "tube" with a section open at both ends. The sheets are typically made of glass, plastic or aluminum oxide, and the spacers of glass, polyvinyl chloride or other plastic. The sheets cover the major surfaces of the gel. A major surface of a gel or cassette is the surface having the largest surface area.

Typically the gel is formed from liquid reagents poured into the cassette in order to achieve close contact between the gel thus created and the walls of the cassette. If the gel is formed by polymerization, then the gel will be in contact with all of the exposed internal surfaces of the cassette as is the case with acrylamide gels. This contact is important because any gaps between the gel and the cassette walls cause defects in the electrophoresis migration. In the case of the SDS-protein electrophoresis procedure, a liquid-filled space offers a localized region of increased conductivity, thereby destroying the symmetry of the electric field necessary to obtain informative patterns of separated proteins. A gas-filled gap gives rise to localized heating, due to the diminished thermal conductivity between the underlying gel and the external wall of the cassette. Due to power dissipated in the gel during passage of the electrophoretic current, good and even thermal conduction from the gel to the cassette walls and then to the surrounding cooling system is highly desirable.

The need to handle slab gels in the cassettes in which they were originally formed leads to a serious problem in that any transportation of gels between the sites of making and use must involve the transportation of the cassette, usually made of glass, which is fragile and heavy. In addition, this may necessitate the use of disposable cassettes in order to avoid the return shipment and cleanup of used cassettes. However, centralized manufacture of slab gels is very desirable as a means of providing a standardized separating medium to dispersed users of electrophoresis separations, and as a means of eliminating the need to produce the gels at the site of use, which is labor intensive.

Sufficiently close contact between gel and cassette is generally not achieved when a preformed slab gel is pressed between two flat sheets of stiff insulator, such as glass, because the pressure applied is generally localized and gaps, usually thin films of liquid, remain between glass and gel at other points. Such films disrupt the electrophoresis and give rise to imperfect separation patterns.

Recently, other investigators (P. Horowitz and S. Bowman, *Electrophoresis.* Vol. 7, pp. 534–535, 1986) have shown that a preformed gel attached by one surface to a flexible plastic backing can be successfully reassembled into a cassette having a pair of rigid glass or alumina walls which enclose the plane of the gel slab by "rolling the wet gel [having a GelBond backing] onto the front glass plate of the gel cassette." (GelBond is a trademark of FMC Corp., Rockland, Me.) The plastic backing effectively serves as one insulating wall of the cassette, and one that is flexible enough to allow any excess liquid to be squeezed from between the gel and the glass plate that forms the other insulating wall during application to the latter. The rolling process is generally accomplished by hand. The GelBond plastic produces no force normal to the plane of the gel slab to ensure that the seal formed during the rolling process is maintained. Therefore, it is not effective as a cassette wall to support a slab electrophoresis gel, and a second glass plate is required behind the GelBond. Clamping the cassette walls closed produces a non-uniform force normal to the surface of the gel slab so that the force is greater at the edges. This encourages the walls to bow outward forming a convex outer surface, allowing the formation of bubbles or free liquid droplets between the gel and plate at the middle of the gel area. The usefulness of the Horowitz system is therefore limited to gels of small size which can be enclosed in cassettes that are not subject to the bowing effect. Further, the plastic backing must be present in the Horowitz system because the gel can only be rolled onto a single rigid surface. This technique is difficult, is progressively more unwieldy for larger gels, and, most importantly, requires that the gel slab be on a plastic backing. Such a backing is expensive, makes the gels more difficult to manufacture, and prevents certain subsequent uses of the gels, such as so-called Western blotting.

SUMMARY OF THE INVENTION

The invention provides a curved surface cassette/gel system for easily and efficiently pressing a slab electrophoresis gel and electrophoresis sample into a cassette. In general, the walls of the cassette and the major surfaces of the gel coact to substantially exclude liquid or gas from between either wall and the major surfaces of the gel by exerting a normal force at all points on the walls of the cassette and at all points on the major surfaces of the gel. In accordance with the invention, either the cassette or the slab gel has at least one curved surface.

In one embodiment, one cassette wall has an inherent curvature in the open position. The curvature is convex as seen from the gel cavity formed between the two cassette walls. The curved wall is elastically deformable so that it can be made to assume a flat position when the cassette is closed. This arrangement provides for sealing of the major surfaces of the gel in contact with the walls of the cassette such that a normal force is exerted at all points on the gel area by the tension in the straightened wall. This force substantially excludes liquid or gas from between either wall and the major surfaces of the gel.

In another embodiment, the cassette may be constructed so that both of the two major walls are convex with respect to the gel cavity inside the cassette. Closing the curved cassette walls against a gel applies pressure at all points across the two major surfaces of the gel from one and to the other. This pressure presses out from the surface of the gel excess liquid which disrupts the normal pattern of electrophoresis and prevents the formation, between the cassette wall and the surface of the gel, of air pockets which disrupt the conduction of heat from the gel.

In both embodiments, this normal force prevents the problem of outward bowing of the cassette wall normally caused by the pressure of latches or clamps applied along one or both sides of the cassette to lock the cassette in the closed position (i.e. to hold the cassette walls together). The outward bowing of the walls of a standard cassette results in air pockets between wall and gel. As gels get larger, the problem of bowing becomes more pronounced in standard cassettes. The curved wall cassettes may be used to house virtually any size gel.

In another embodiment, a slab electrophoresis gel may be produced on which one or both major surfaces are convex. By the principle applied above, when a flat cassette wall is closed on the convex surface of a gel, the convex surface is pressed flat and any excess liquid on the surface of the gel is pressed out and the formation of air pockets is prevented. The pressure developed between the flat walls of the closed cassette and the convex surface(s) of the gel ensures tight apposition of gel and cassette as required for good results.

In another embodiment, a flat surface gel may be placed over a wall forming a rigid convex surface. An elastically deformable wall may be stretched over the gel to exert a normal force across all points on the major surfaces of the gel.

In another embodiment, the cassette walls are inflatable with a fluid capable of conducting heat from the gel. Inflation of the cassette walls exerts a normal force across the major surfaces of the gel.

In another embodiment, the headpiece of the cassette is divided by septa to form a series of channels through which sample material is conducted into the adjacent slab gel.

In general, therefore, the present invention utilizes the force exerted normal to the plane of the gel slab by the interaction of two cassette walls and a gel slab, at least one of which has at least one curved surface which is deformed upon closing the cassette. When a wall of the cassette is straightened, the wall exerts a force against the surface over which it is straightened. The geometry of the sheet can be made so as to exert a force normal to the surface of the gel, and this force can be substantially uniform over the entire gel area. Likewise, the closing of flat cassette walls . against a convex-surface gel slab can achieve the same effect.

The present invention uses this normal force to squeeze the gel slab between two sheets of material, forming a seal between the two sheets and the gel and securing the gel in position to prevent the formation of bubbles, surface liquid droplets, and the like, between the gel and either wall. Such squeezing is generally necessary with larger gels. If a gel slab is run in a loose cassette, regions of surface liquid form between the gel and the sheet which disturb the electric field and cause unsatisfactory electrophoretic separation. The use of a force normal to the gel slab surface produces pressure at all points on the gel area. For this reason, and because it is unnecessary to support the gel by hand during the rolling process in order to form a seal between the gel and the wall, the present invention is contemplated for use with virtually any size gel.

By making use of a "hinge" (or "head-piece") joining the two walls of the cassette at one edge, the invention also provides a possible site for the application of liquid or solid samples along an edge of the slab, in position for subsequent electrophoresis through the plane of the slab. Placing a sample in the head-piece, followed by introduction of the slab and closure of the cassette ensures tight apposition between the sample and the slab. This arrangement also makes sample application more convenient, particularly in two-dimensional electrophoretic procedures.

The invention provides a cassette/gel system not only for the electrophoresis step, but also for storage, optical scanning of gels, and various other uses.

BRIEF DESCRIPTION OF THE DRAWINGS

The various advantages and novel aspects of the present invention will be more readily apparent from the following brief description when read in conjunction with the appended drawings, in which.

DETAILED DESCRIPTION OF THE PREFERRED EMBODIMENTS

Figure 1:
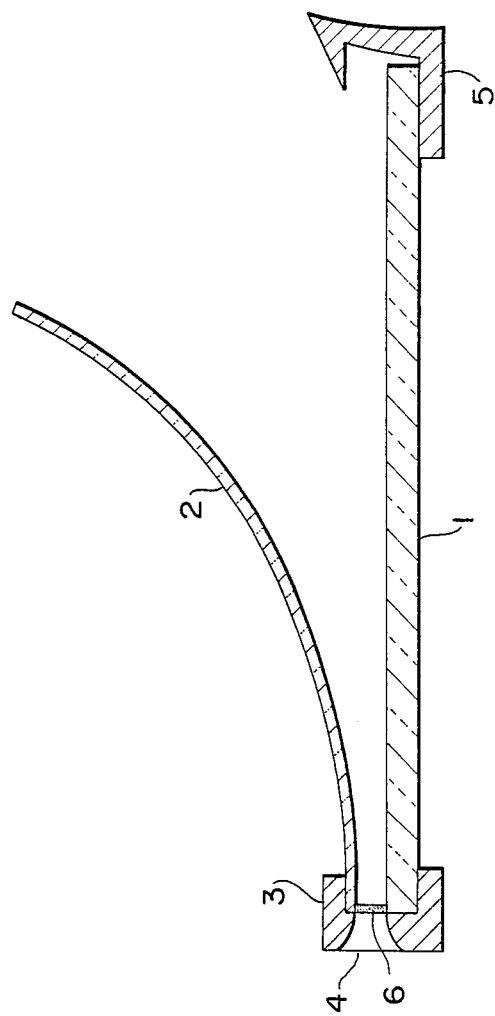
FIG. 1 is an illustration of a slab electrophoresis gel cassette in accordance with a first embodiment of the invention, shown in the open position and having a single convex wall.

The construction and use of a preferred embodiment of the invention is illustrated in FIGS. 1 through 14. Referring first to FIG. 1, the major walls i and 2 of the cassette each consist of thermally conductive, waterproof, insulating material that is either flat and rigid, or thinner, flexible and curved, and is elastically deformable to form a substantially flat wall. Wall 1 may be made of thick glass, aluminum oxide, beryllium oxide and the like. Wall 2 may be made of thinner glass, fiberglass composite material, polycarbonate, polymethylmethacrylate, polystyrene and the like.

Wall 2 is formed as a section of a cylinder whose axis extends perpendicular to the plane of the drawing. The curvature of wall 2 is preferably convex as seen from the gel cavity inside the cassette and is such that the rectangular wall forms a portion of a cylindrical surface with two edges parallel to the axis of the cylinder and two edges forming circular circumferential areas.

Walls 1 and 2 may be attached to each other or to a straight headpiece 3 along any straight edge. A straight headpiece 3 attached to one straight edge of each of walls 1 and 2 contains a channel 4 which allows passage of an electric current through the headpiece 3 and into the gel slab (not shown in FIG. 1) located between walls 1 and 2. A strip 6 of porous material is used to prevent the gel rod containing the sample from being squeezed through the headpiece of the closed cassette and may be attached to one edge of each wall 1 and 2 in the absence of a headpiece.

Some force is required to hold the cassette in the closed position. This force is required to overcome the spring-like tension of the curved wall 2 when it has been straightened to lie flat against or parallel to the rigid wall 1. This force may be provided by a simple mechanical latch 5 or by a magnet whose short range attractive force locks walls 1 and 2 together when they are brought into close proximity. One or more latches or other closure devices may occur at appropriate places along the cassette.

Figure 2:
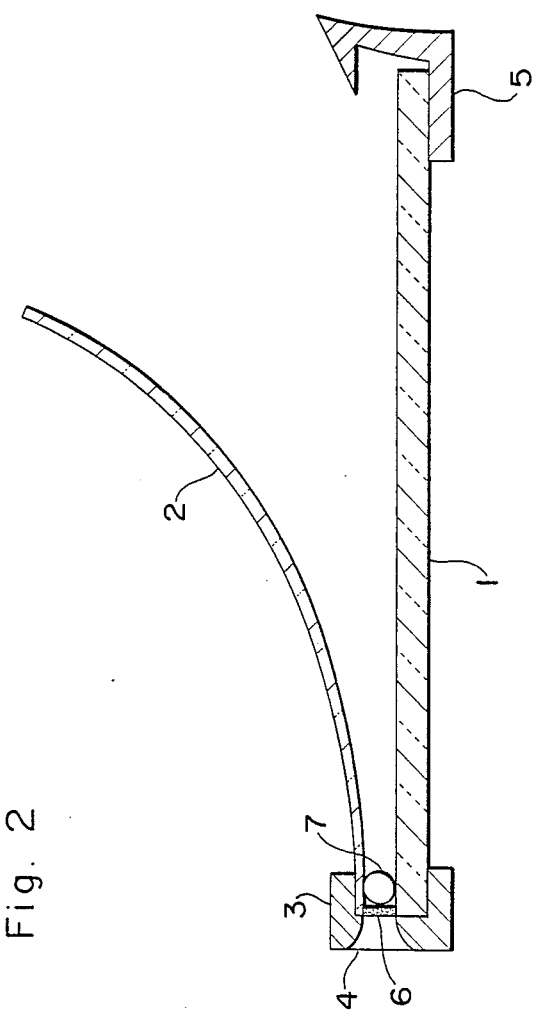
FIG. 2 is an illustration of the gel cassette in the open position with a gel rod (sample) in place.

Referring to FIG. 2, a sample to be separated, such as those contained in a gel rod 7, can be placed between walls 1 and 2 and against the porous strip 6. A gel rod is used as the first dimension of a two-dimensional electrophoretic separation. The sample can also be placed on the latch end of the cassette if it is desirable.

Figure 3:
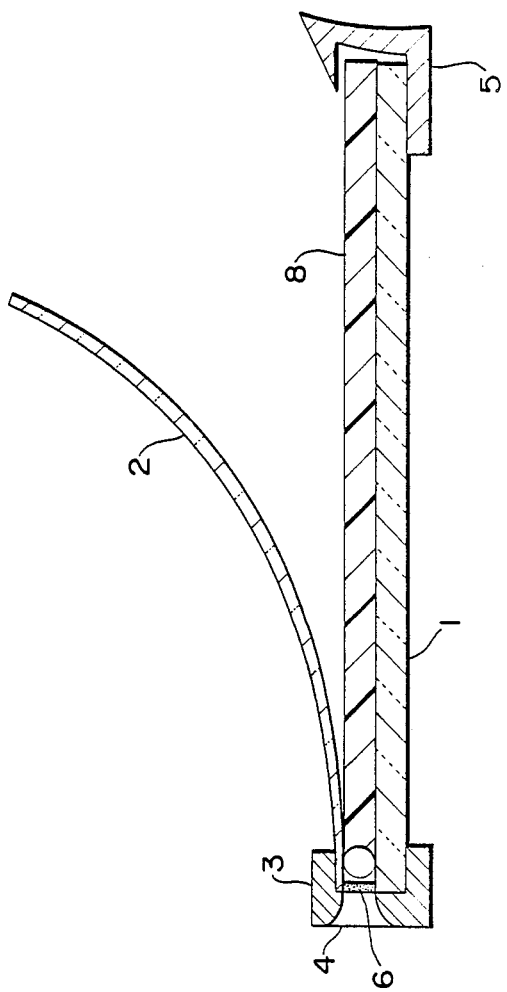
FIG. 3 is an illustration of a the gel cassette in the open position and containing an electrophoresis sample and a slab electrophoresis gel.

Subsequently, a gel slab 8 can be introduced into the cassette as illustrated in FIG. 3. The gel slab 8 may lie on either wall 1 or 2 but preferably lies on the flat wall 1. The gel slab 8 is positioned so as to press the gel rod 7 firmly against the porous strip 6.

Figure 4:
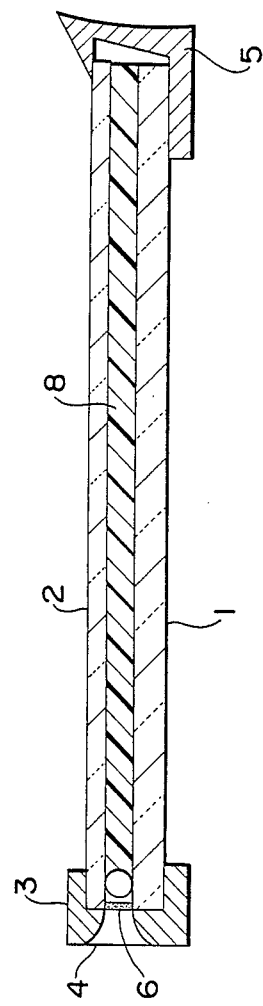
FIG. 4 is an illustration of the gel cassette, sample and gel, with the convex cassette wall straightened into the closed position.

When the cassette is closed, as shown in FIG. 4, the flexible wall 2 is bent down to lie flat upon the slab gel 8, and is latched into position by the latch 5. The cassette and slab gel are now ready for electrophoresis. A conductive path is provided through the channel 4 in the headpiece 3, through the porous strip 6, through the rod gel 7, and then through the slab gel 8 and out into solution around the latch 5.

Figure 5:
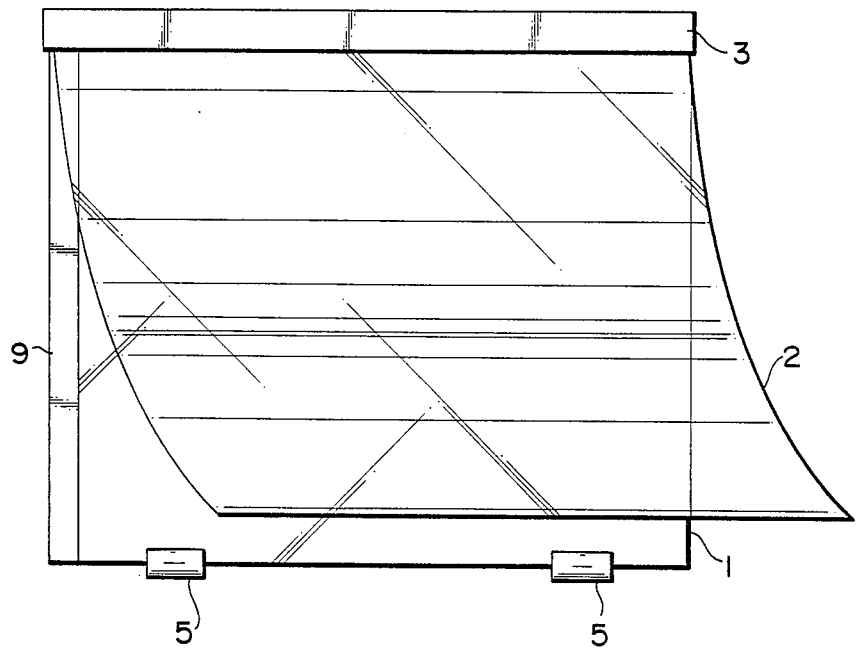
FIG. 5 is an illustration of a modified gel cassette with side spacers to prevent conduction of electric current out of the plane of the gel.

Conduction out of the plane of these figures may be prevented by inclusion of a spacer 9, shown in FIG. 5, along at least one edge of the flat wall perpendicular to the headpiece 3. The spacer may be made of glass or plastic, as in conventional gel cassettes, provided that it matches the thickness of the gel precisely. If gel thickness may vary slightly, then spacers of a compressible material such as silicone rubber foam may be used.

A single spacer may be used when one edge of the cassette is above the liquid level of the conducting buffer. The absence of a spacer on one edge of the cassette also allows easier introduction and removal of the gels. If spacers are required on both edges, the width of the slab gel must be precisely matched to the cassette, or else the spacers must be capable of some lateral movement so as to lie close alongside the edge of the slab.

Figure 6:
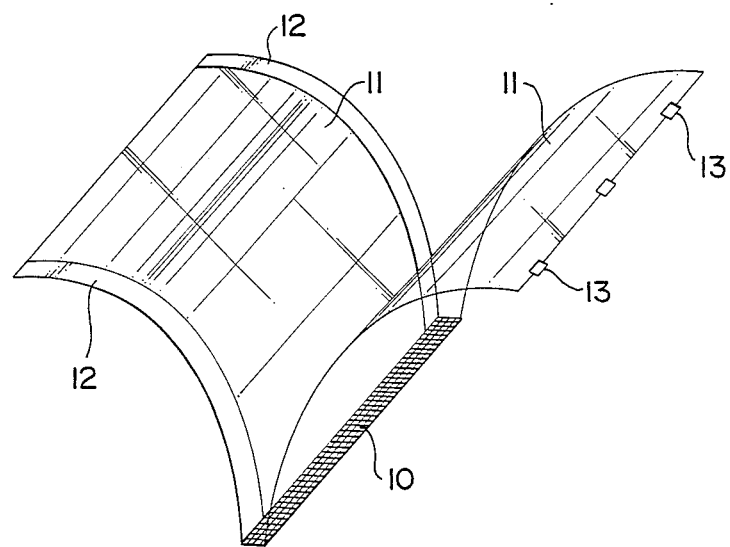
FIG. 6 is an illustration of the slab electrophoresis gel cassette in accordance with a second embodiment of the invention, shown in the open position and having two convex walls.

A second embodiment of the invention is shown in FIG. 6. In this embodiment both walls 11 of the cassette are curved, and may be molded together with the "spine" 10 as a single piece of plastic. The spine consists of a meshwork, or is otherwise porous, thereby allowing passage of current from outside buffer into the gel slab, as well as fulfilling the spine's mechanical functions of joining the two cassette walls and supporting the gel rod sample adjacent to the slab. The walls 11, molded in their curved, relaxed configuration, exert inward force on the gel slab when the cassette is closed and the walls 11 are under tension. A latch mechanism 13 similar to the catch closure on small molded plastic boxes may be used to keep the cassette closed. Spacers 12 preventing the flow of current through the sides of the cassette are made of silicone rubber foam cord threaded through holes molded into the cassette. These cords are easily compressed, and being of slightly larger diameter than the thickness of the slab gel, they will be compressed by closure of the cassette to give an electrically tight 0-ring type seal. An advantage of this embodiment is its low cost of production and the lack of assembly operations required in its manufacture.

Figure 7:
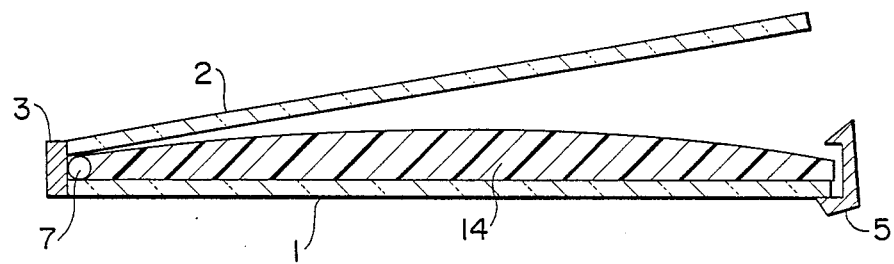
FIG. 7 is an illustration of a third embodiment of the invention, in which the slab electrophoresis gel has convex major surfaces.
Figure 8:
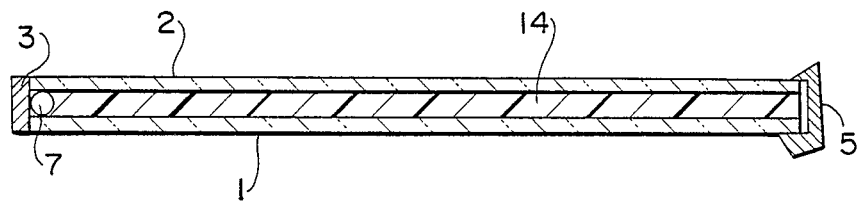
FIG. 8 is an illustration of the third embodiment in which the cassette walls are closed over the convex major surface of the gel.

A third embodiment of the invention is shown in FIGS. 7 and 8. In this embodiment, one or both major surfaces of the gel slab 14 are convex, as shown in FIG. 7. This novel configuration of a gel slab allows the use of a force normal to the surface area of the gel slab to produce a squeezing force that will seal the gel surfaces against the cassette walls and maintain the normal force throughout the gel slab area. When either or both major surfaces of a gel slab are in a convex configuration, either cassette wall or the gel, or both, are deformed when the cassette is closed, FIG. 8. In either case, the deformation or bending is elastic and produces the desired squeezing and sealing effect as described above.

Figure 9:
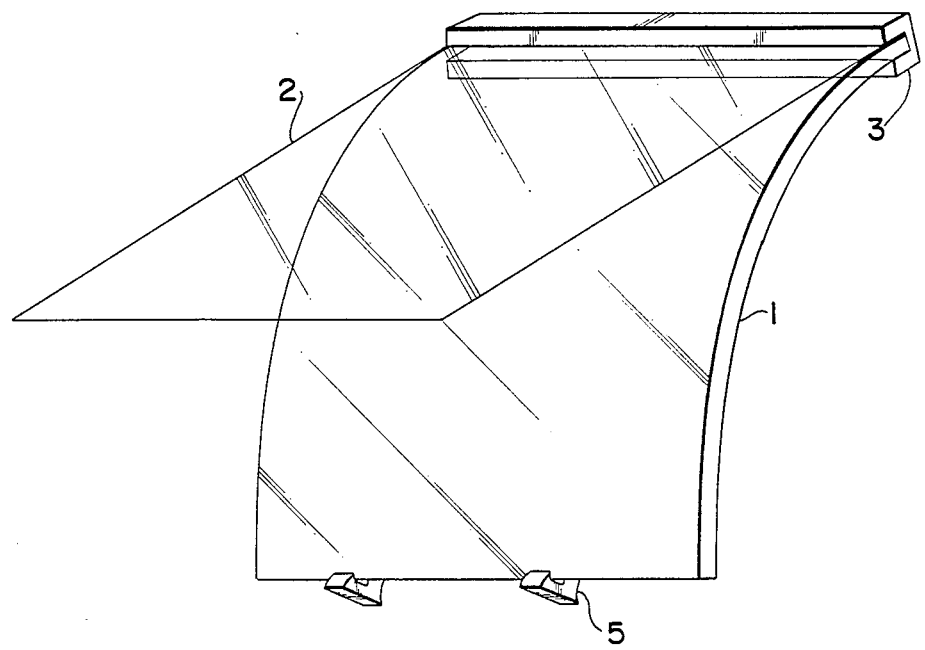
FIG. 9 is an illustration of a slab electrophoresis gel cassette in accordance with a fourth embodiment of the invention, shown in the open position, having a rigid curved wall and a flat deformable wall.

A fourth embodiment of the invention is shown in FIG. 9. In this embodiment wall 1 is rigid and curved. Wall 2 is flat or curved away from wall 1 and elastically deformable so that it can be made to conform to the curve (of wall 1 upon closing the cassette. The cassette might be constructed by sliding wall 2 into the headpiece 3. The headpiece 3 might be constructed so that it can be open enough to allow wall 2 to slide into it then close down on wall 2 to retain it. Wall 2 can be attached to the slab electrophoresis gel prior to constructing the cassette. Wall 2 may also be permanently attached to the headpiece 3. A gel slab 8 as shown in FIG. 3 can then be introduced into the cassette.

When the cassette is closed, the flexible wall 1 is bent down or stretched over the gel slab and is held in position by the latch 5.

The headpiece 3 is constructed so that a sample 7 of material to be separated, shown in FIG. 2, can be placed in contact with the gel slab 8. The sample 7 to be separated in a two-dimensional gel is usually confined in a semi-solid medium.

Figure 10:
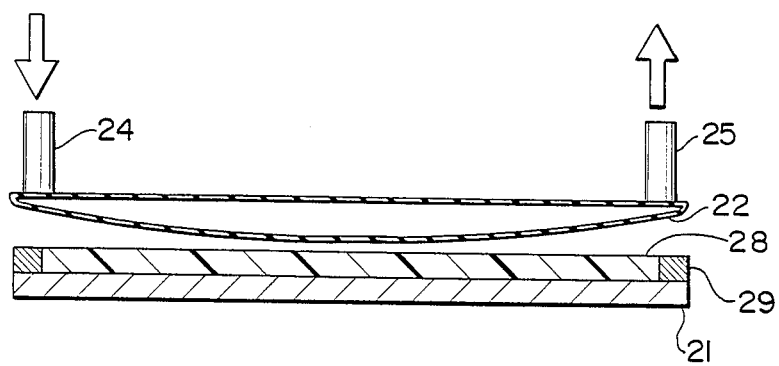
FIG. 10 is an illustration of a slab electrophoresis gel cassette in accordance with a fifth embodiment of the invention, shown in the open position, having inflatable walls.
Figure 11:
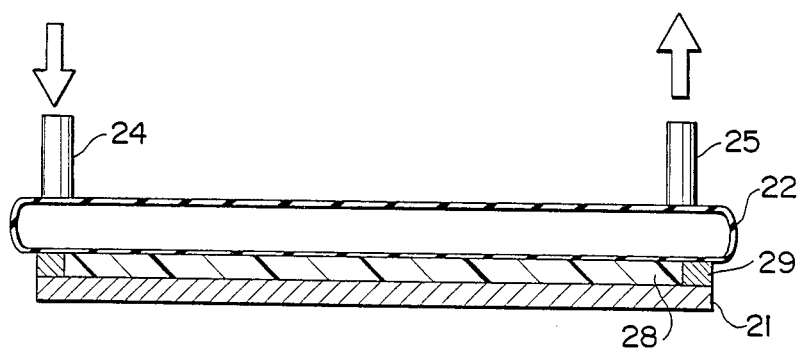
FIG. 11 is an illustration of the fifth embodiment of the invention, shown in the closed position.

A fifth embodiment of the invention is shown in FIGS. 10 and 11. In this embodiment, the cassette comprises a rigid wall 21 and an inflatable wall 22. The inflatable wall is essentially a bag which when inflated against a major surface of a gel, as in FIG. 11, applies a normal force which substantially excludes liquid or gas from between either wall and the major surfaces of the gel. The rigid wall 21 acts as a base plate on which a slab-shaped gel 28 sets. Spacers 29 occur on each side of the base plate. An inflatable coolant bag functions as one inflatable wall 22. Cooling fluid is supplied to the inflatable wall 22 by the inlet port 24 and drawn away through the outlet port 25. Cooling fluid may be applied to the inflatable wall 22 prior to electrophoresis or continuously during electrophoresis. In the alternative, both walls 21 and 22 may be inflatable.

Figure 12:
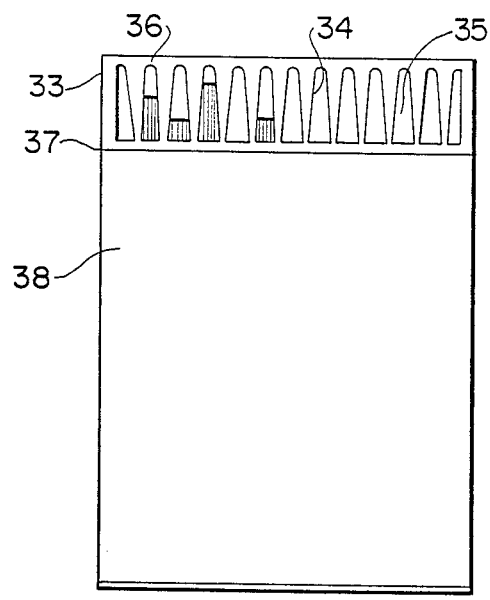
FIG. 12 is an illustration of a slab electrophoresis gel cassette in accordance with a sixth embodiment of the invention showing a headpiece divided into a series of channels.
Figure 13:
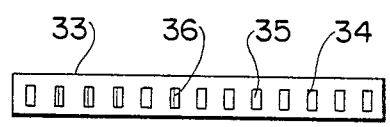
FIG. 13 is an illustration of the sixth embodiment in top view.
Figure 14:
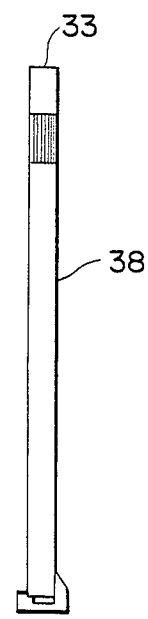
FIG. 14 is an illustration of the sixth embodiment in side view.

A sixth embodiment of the invention is shown in FIGS. 12, 13 and 14. FIG. 12 shows a headpiece 33 divided by septa 34 to form a series of channels or wells 35 into which sample material 36 may be placed. The septa 34 may be "V" shaped to form a knife edge seal 37 at the slab gel 38 to prevent cross-flow between the wells 35 that may occur if the septa 34 do not tightly abut the slab gel 38. FIG. 13 shows a top view of headpiece 33 with septa 34 dividing it into wells 35 into which sample material 36 are placed. FIG. 14 shows a side view of the headpiece 33 and slab gel 38 shown in FIG. 12.

While the invention has been disclosed by reference to the details of preferred embodiments, the disclosure is intended in an illustrative rather than in a limiting sense, as it is contemplated that modifications will readily occur to those skilled in the art, within the spirit of the invention and the scope of the appended claims.

What is claimed is:

1. A slab-shaped electrophoresis gel in a cassette comprising:
   a slab-shaped electrophoresis gel having two major surfaces; and
   a cassette for containing a slab-shaped electrophoresis gel, the cassette having first and second walls, the walls having closed and open positions and means for joining them at one edge;
   the first and second walls defining a gel cavity therebetween when in the closed position and the gel being placed between the walls;
   whereby the walls of the cassette and the major surfaces of the gel coact to exert at all points on the walls and at all points on the gel's major surfaces a substantially uniform normal force which substantially excludes liquid or gas from between either wall and the major surfaces of the gel.

2. A cassette for containing a slab-shaped electrophoresis gel comprising:
   first and second walls having closed and open positions and means for joining said walls at one edge;
   said first wall being rigid and said second wall being elastically deformable;
   said first and second walls defining a gel cavity therebetween and being adapted to exert at all points on the gel's major surfaces a normal force which substantially excludes liquid or gas from between either wall and said major surfaces when placed in the closed position; and
   said first wall being flat and said second wall being convex as seen from between said walls when placed in the open position.

3. The cassette of claim 2 wherein said first and second cassette walls are comprised of a waterproof, electrically insulating and thermally conducting material.

4. The cassette of claim 2 wherein the means for joining comprises a strip of porous material attached to said one edge of said first and second walls.

5. The cassette of claim 2 wherein the means for joining comprises a headpiece attached to said one edge of said first and second cassette walls.

6. The cassette of claim 5 further comprising a channel for allowing passage of electric current through said headpiece.

7. The cassette of claim 6 wherein said channel is divided by septa into individual wells for application of individual samples to be separated.

8. The cassette of claim 2 further comprising a means for holding said first and second cassette walls in the closed position.

9. The cassette of claim 8 wherein the means for holding is either mechanical or magnetic.

10. The cassette of claim 2 wherein said first cassette wall is comprised of material selected from the group consisting of glass, aluminum oxide and beryllium oxide.

11. The cassette of claim 2 wherein said second cassette wall is comprised of material selected from the group consisting of glass, fiberglass composite, polycarbonate, polymethacrylate and polystyrene.

12. A cassette for containing a slab-shaped electrophoresis gel, comprising:
    first and second walls having closed and open positions and means for joining said walls at one edge;
    said first and second walls defining a gel cavity therebetween and being adapted to exert at all points on the gel's major surfaces a normal force which substantially excludes liquid or gas from between either wall and said major surfaces when placed in the closed position; and
    said first and second walls being elastically deformable and convex as seen from between said walls when placed in the open position.

13. The cassette of claim 12 wherein the means for joining comprises a spine attached to said one edge of said first and second cassette walls.

14. The cassette of claim 13 wherein the spine is a porous material.

15. In a cassette for containing a slab-shaped electrophoresis gel having first and second cassette walls, the improvement comprising a headpiece having a channel for allowing passage of electric current through said headpiece and a strip of porous material for preventing passage out of the cassette through said headpiece of the slab gel or a sample to be separated, said headpiece joining said walls at one edge; and
    at least one of said first and second walls being elastically deformable and curved outwardly with respect to the other cassette wall when the cassette is in an open position; and
    said first and second walls defining a gel cavity therebetween and being adapted to exert at all points on the gel's major surfaces a normal force which substantially excludes liquid or gas from between either wall and said major surfaces when the cassette is in a closed position.

16. A cassette for containing a slab-shaped electrophoresis gel, comprising:
first and second walls having closed and open positions and means for joining said walls at one edge;
a headpiece for connecting said first and second walls, said headpiece being comprised of a channel for allowing passage of electric current through said headpiece, and enclosing a strip of porous material for preventing passage out of the cassette through the headpiece of the electrophoresis gel or a sample, said headpiece being attached to one edge of each first and second wall;
said first and second walls defining a gel cavity therebetween and being adapted to exert at all points on the gel's major surfaces a normal force which substantially excludes liquid or gas from between either wall and said major surfaces when placed in the closed position; and
at least one of said walls being elastically deformable and convex as seen from between said walls when placed in the open position.

17. A method of exerting a normal force at all points on the major surfaces of a slab-shaped electrophoresis gel, comprising:
placing a slab-shaped electrophoresis gel into a cassette having at least one wall which is curved away from the gel when the cassette is in an open position and is elastically deformable; and
closing the cassette by causing the curved wall to assume a flat conformation.

18. A method of exerting a normal force at all points on the major surfaces of a slab-shaped electrophoresis gel, comprising:
placing a slab-shaped electrophoresis gel having at least one convex major surface into a cassette having either flat or curved and elastically deformable walls; and
closing the cassette to exert at all points on the gel's major surfaces a normal force which substantially excludes liquid or gas from between either wall and said major surfaces.

19. An electrophoresis gel and cassette, comprising:
(a) a slab-shaped electrophoresis gel having first and second major surfaces; and
(b) a cassette for containing the gel having first and second walls and means for joining said walls at one edge, at least one wall being convex as seen from between said walls, said cassette having an open position and a closed position.,
whereby placing the gel between said walls and closing the cassette (a) brings the first and second walls into parallel conformation and (b) exerts at all points on the gel's first and second major surfaces a normal force which substantially excludes liquid or gas from between either wall and said major surfaces.

20. An electrophoresis gel and cassette, comprising:
(a) a slab-shaped electrophoresis gel having first and second major surfaces, at least one surface being convex; and
(b) a cassette for containing the gel having first and second walls and having means for joining said walls at one edge and having an open position and a closed position;
whereby placing the gel between the walls and closing the cassette exerts at all points on the gel's first and second major surfaces a normal force which substantially excludes liquid or gas from between either wall and said major surfaces.

21. The gel and cassette of claim 20 wherein at least one wall of the cassette is convex as seen from between the walls when the cassette is in the open position.

22. A cassette for containing a slab-shaped electrophoresis gel, comprising:
first and second walls having open and closed positions and means for joining said walls at one edge, at least one wall being inflatable; and
said walls being adapted to exert at all points on the gel's major surfaces a normal force which substantially excludes liquid or gas from between either wall and said major surfaces when the walls are inflated against the gel.

23. The cassette of claim 22 wherein said inflatable wall is inflatable to form a curved surface in the direction of the gel cavity.

24. The cassette of claim 22 wherein said normal force is generated by fluid pressure inside said inflatable wall.

25. The cassette of claim 22 wherein
said inflatable wall comprises a surface shared by the gel cavity and a chamber filled or fillable with fluid; and said normal force is generated by fluid pressure inside said chamber against said inflatable wall.

* * * * *